United States Patent [19]

Kreyenhagen

[11] Patent Number: 5,330,522
[45] Date of Patent: Jul. 19, 1994

[54] RING ELECTRODE FOR A MULTILUMEN LEAD AND METHOD OF CONSTRUCTING A MULTILUMEN LEAD

[75] Inventor: Paul E. Kreyenhagen, Redmond, Wash.

[73] Assignee: Siemens Pacesetter, Inc., Sylmar, Calif.

[21] Appl. No.: 997,804

[22] Filed: Dec. 29, 1992

[51] Int. Cl.⁵ ............................................. A61N 1/04
[52] U.S. Cl. ............................................. 607/122
[58] Field of Search ............................. 128/784, 786

[56] References Cited

U.S. PATENT DOCUMENTS

| | | | |
|---|---|---|---|
| 4,161,952 | 7/1979 | Kinney et al. | 128/786 |
| 4,328,812 | 5/1982 | Ufford et al. | 128/786 |
| 4,413,636 | 11/1983 | Jasso | 128/786 |
| 4,944,088 | 7/1990 | Doan et al. | 29/858 |
| 4,947,866 | 8/1990 | Lessar et al. | 128/784 |

Primary Examiner—William E. Kamm
Attorney, Agent, or Firm—Malcolm J. Romano; Lisa P. Weinberg

[57] ABSTRACT

An implantable pacing lead for use with a cardiac pacemaker having a multilumen tubing for the lead body and at least one ring electrode or electrical contact located between the distal and proximal ends of the pacing lead. The ring electrode includes axially aligned bores therethrough, the bores corresponding to the locations of the lumens within the multilumen tubing. A stabilizing element assures that the interconnection between the multilumen tubing and the cylindrical electrode is secure.

19 Claims, 2 Drawing Sheets

RING ELECTRODE FOR A MULTILUMEN LEAD AND METHOD OF CONSTRUCTING A MULTILUMEN LEAD

BACKGROUND OF THE INVENTION

This invention relates generally to an implantable pacing lead for use with a cardiac pacemaker, and more specifically, to a pacing lead having a multilumen tubing for the lead body and at least one ring electrode or electrical contact located between the distal and proximal ends of the pacing lead.

Medical science has advanced the state-of-the-art of pacemakers and cardiac pacing, and the associated pacing leads, to the point where pacing leads requiring three or more electrical conductors are now in common use. In some instances, the electrical conductors are attached to ring electrodes spaced anywhere from a few millimeters to several centimeters behind the distal end of the pacing lead, and to electrical contacts at the proximal end of the lead. The electrodes may be used, for example, as the cathode or anode in a bipolar pacing configuration, or alternatively, as sensory electrodes to sense parameters, such as atrial electrical activity; ventricular electrical activity; and impedance changes to determine such parameters as cardiac stroke volume, respiration rate, or minute volume.

Various configurations have been proposed for assembling in-line or ring electrodes and electrical contacts, and for interconnecting them to conductors extending between the proximal and distal ends of the pacing lead. It has been known, for example, to use a multilumen silicone tube which is generally an elongated length of silicone tubing having multiple axially aligned channels or lumens extending therethrough. When the multilumen tubing is assembled with other components of the system, the individual conductors are inserted into the lumens of the multilumen tubing, and advanced to their point of interconnection to their respective electrodes/terminals.

At the point of interconnection of the multilumen tubing and a ring electrode or connector, it is necessary to provide a secure electrical connection between the conductor and the ring electrode, as well as to provide an assembly which will prevent invasion of body fluids into the lumens. Invasion and retention of body fluids within the lumens of the lead body threatens the viability and integrity of the pacing lead. This can be manifest, as in one example, by body fluid electrolytes entering the lead body and causing electrical shorting between conductors and/or electrodes.

Multilumen tubing has advantages with respect to its flexibility and biocompatibility which makes it particularly suitable for use in the construction of a pacing lead. Thus, a high integrity interconnection between the multilumen tubing and ring electrode is desirable.

The intended environment for the pacing lead, i.e. implanted within the body and inserted through a vein and on into the heart, subjects the pacing lead to repetitive flexure. This environment dictates that the interconnection of a ring electrode and the multilumen tubing of the lead body, as well as the electrical connection between the ring electrode and its respective conductor, will endure the repetitive flexure. Invasion of blood fluids about the edges of the ring electrode and into the lumens of the multilumen tubing must be prevented. In addition, electrical conductors which pass through the ring electrode must be electrically isolated from the ring electrode. Accordingly, the configuration of the interconnection point for a ring electrode and a multilumen tubing lead body is of critical importance.

SUMMARY OF THE INVENTION

The present invention details a pacing lead for use with a cardiac pacemaker which includes a multilumen lead body having a plurality of lumens axially positioned within a flexible, biocompatible tubing material and a method for its construction. The multilumen tubing is severed to allow insertion of a cylinder of electrode material which forms the ring electrode. The cylinder of electrode material includes axially aligned bores therethrough, the bores corresponding to the locations of the lumens within the multilumen tubing. A stabilizing element assures that the interconnection between the multilumen tubing and the cylindrical electrode is secure. In addition, the electrical conductors which pass through the cylindrical electrode are protected by a cylindrical insulating element. Finally, a connector pin provides the interconnection between the cylindrical electrode and its respective conductor.

DETAILED DESCRIPTION OF THE PREFERRED EMBODIMENT

Figure 1:
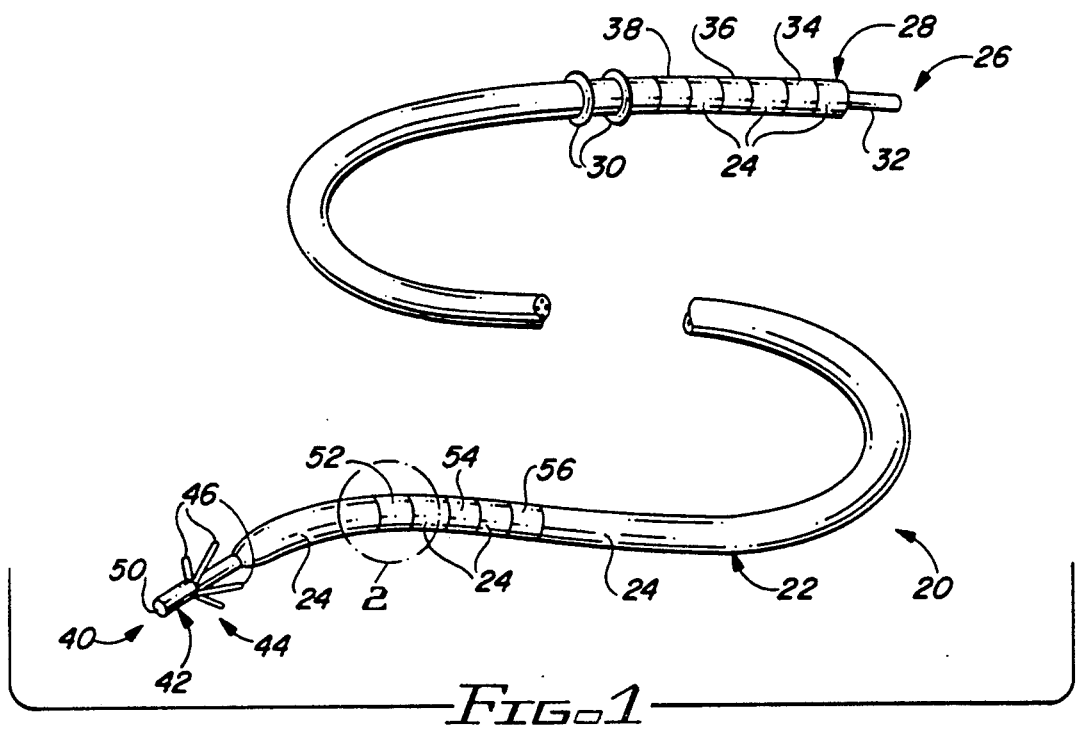
FIG. 1 depicts a pacing lead having a multilumen tubing and at least one ring electrode constructed according to the description of the present invention.

FIG. 1 shows a pacing lead 20 according to the present invention. The pacing lead 20 has an elongated lead body 22 which includes electrical conductors extending through lumens within a multilumen tubing 24. The multilumen tubing 24 is preferably fabricated of silicon rubber, polyurethane or another suitable insulative material having the properties of biocompatibility, biostability and flexibility.

At a proximal end 26 of the pacing lead 20 is a connector assembly 28 which is provided with sealing rings 30 and which includes a terminal pin 32 and ring terminals 34, 36 and 38. The portions of the connector assembly 28 spacing-apart the ring terminals 34, 36 and 38 may be fabricated from segments of multilumen tubing of silicon rubber, polyurethane or other suitable insulative plastic, assembled in the manner discussed herein below. The terminal pin 32 and ring terminals 34, 36 and 38 are preferably fabricated of a stainless steel or other suitable conductive material.

At a distal end 40 of the pacing lead 20 is an electrode assembly 42. A tine sheath 44 which includes a plurality of individual tines 46 may be located immediately proximal to a tip electrode 50 at the distal end 40 of the electrode assembly 42. Pliant tines 46 engage the endocardial tissue and urge the tip electrode 50 into contact with the endocardium following implantation in a direction parallel to the axis of electrode assembly 42.

A number of ring electrodes 52, 54 and 56 are shown spaced proximally from the distal end 40 of the pacing lead 20. The ring electrode 52 may be used, for example, as an anode in a bipolar pacing system. Alternatively, the ring electrodes 52, 54 and 56 can be used as sensor electrodes to determine various parameters of endocardial activity, such as atrial electrical activity, ventricular electrical activity, or to sense impedance changes to determine stroke volume, pre-ejection fraction, minute volume and respiratory rate. Monitoring of these parameters is beneficial for advanced pacing systems to allow the pacemaker to more effectively respond to and control cardiac activity. It should be noted that a pacing lead may have one or more electrodes embodying the concepts of the present invention, limited only by the number of available lumens in the multilumen tubing 24.

Short segments of multilumen tubing 24 may be used to form the lead body 22 between the respective ring terminals 34, 36 and 38, as well as between the ring electrodes 52, 54 and 56. The present invention addresses the assembly and joining of the ring electrodes 52, 54, 56 or ring terminals 34, 36, 38 to the multilumen tubing 24, and the electrical terminal connections with the respective electrical conductors which terminate at the electrodes or conductors.

Figure 2:
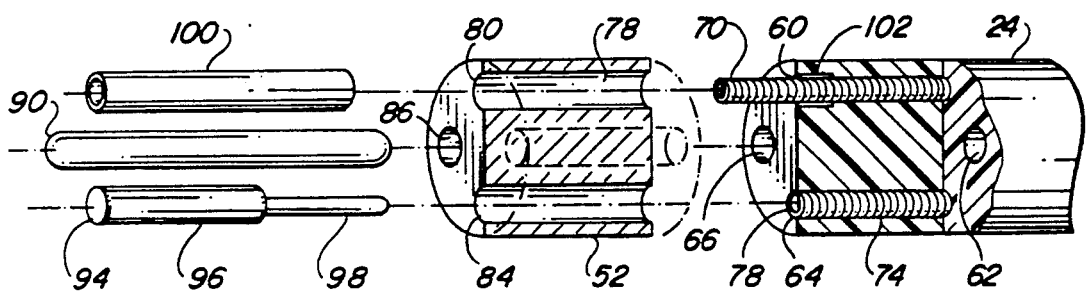
FIG. 2 is a partially cross-sectional, exploded view of a portion of FIG. 1, depicting the connection between the multilumen tubing and a ring electrode according to the present invention.

FIG. 2 depicts a detailed exploded view of the area about electrode 52 depicting the interconnection of the multilumen tubing 24 and the ring electrode 52. It may be understood that the design shown in FIG. 2 and described below can also be incorporated for the ring electrode 54, as well as for the ring terminals 34 and 36. For reasons discussed below, a different design incorporating similar fundamental components may be required for the ring terminal 38 or ring electrode 56 if there are an equal number of conductors and lumens at the point of connection to the ring electrode 56 or ring terminal 38.

As shown in FIG. 2, the multilumen tubing 24 has a generally cylindrical cross-section and four lumens 60, 62, 64 and 66, which are spaced-apart and axially aligned to extend along the length of the multilumen tubing 24. The lumens 60, 64 provide enclosed pathways for electrical conductors 70 and 74. For purposes of the following description, it may be appreciated that conductors 72 and 76 (not shown) located within lumens 62 and 66 have been coupled to the electrodes 54 or 56 (FIG. 1) of the pacing lead 20, proximally of the ring electrode 52. Also, it should be noted that conductor 70 passes through the ring electrode 52 and is electrically connected to the tip electrode 50 and the terminal pin 32.

The electrical conductors 70, 72, 74 and 76 are preferably helical coils which, when inserted through the respective lumens 60, 62, 64, 66, define an internal chamber or passageway 78. One of these passageways 78 may allow for the insertion of a stiffening guidewire stylet (not shown) which allows the physician to insert and guide the pacing lead 20 through the vein(s) into the heart (not shown). However, the passageway 78 also provides a conduit susceptible to the invasion of body fluids if the integrity of the connection between the multilumen tubing 24 and the electrode 52 is not maintained.

The ring electrode 52, depicted partially in phantom, is a generally cylindrical solid element having four bores 80, 82, 84 and 86, drilled therethrough. The bores 80, 82, 84 and 86 are positioned to coaxially align with the lumens 60, 62, 64 and 66, respectively, of the multilumen tubing 24. The ring electrode 52 is preferably formed from an electrically conductive, yet biocompatible material, such as stainless steel, MP-35N, Elgiloy, titanium, platinum-iridium, gold, silver, carbon, or other suitable material.

As further illustrated in FIG. 2, a means for interconnecting and affixing the ring electrode 52 to the multilumen tubing 24 is depicted. Preferably, this includes a stabilizing element 90, which is a cylindrical rigid element having a length greater than the axial length of the ring electrode 52. The stabilizing element is inserted through the bore 86 of ring electrode 52 and extends from the opposite faces thereof into the lumen 66 of the abutting multilumen tubing 24. The stabilizing element 90 enhances the interconnection between the ring electrode 52 and the multilumen tubing 24, and is secured to both of these elements by an appropriate adhesive or by welding. The stabilizing element 90 may be formed from a metallic material compatible with the ring electrode material, or may be formed from an appropriate rigid composite or plastic material.

A connector pin 94 is depicted as inserted into the bore 84 of the ring electrode 52. A head portion 96 of the connector pin 94 has an outer diameter which closely matches the inner diameter of the bore 84 to provide a secure interference fit, electrical contact. Alternatively, the pin 94 can be laser welded to the ring electrode 52. The connector pin 94 also has a tail portion 98 which extends from the head portion 96 into the passageway 78 defined by the electrical conductor 74 within lumen 64 of the multilumen tubing 24. The tail 98 is electrically joined to the conductor 74, either by crimping or by welding.

The means for interconnecting and affixing the ring electrode 52 and multilumen tubing 24 may also be defined by or include a cylindrical insulating element 100, passing through bore 80 of the ring electrode 52. The cylindrical insulating element 100 allows pass-through of the electrical conductor 70 through the ring electrode 52 without electrical contact or shorting of the conductor 70 to the ring electrode 52. The cylindrical insulating element 100 may have a length equal to the axial length of the ring electrode 52. However, it is preferable that the cylindrical insulating element 100 extends from the ring electrode 52 in either or both directions and is inserted into a receiving cylindrical bore 102 formed in the facing ends of the multilumen tubing 24, coaxially with the lumen 60.

When the ring electrode 52, multilumen tubing 24, stabilizing element 90, connector 94, and cylindrical insulating element 100 are assembled, they are bonded together with an appropriate glue or cement. Moreover, by the construction depicted and illustrated herein, the connections between the facing ends of the ring electrode 52 and the multilumen tubing 24 are maintained by the stabilizing element 90 as well as the cylindrical insulating element 100, which extend from the ring electrode 52 into the respective lumens 66, 60 of the multilumen tubing 24.

Figure 3:
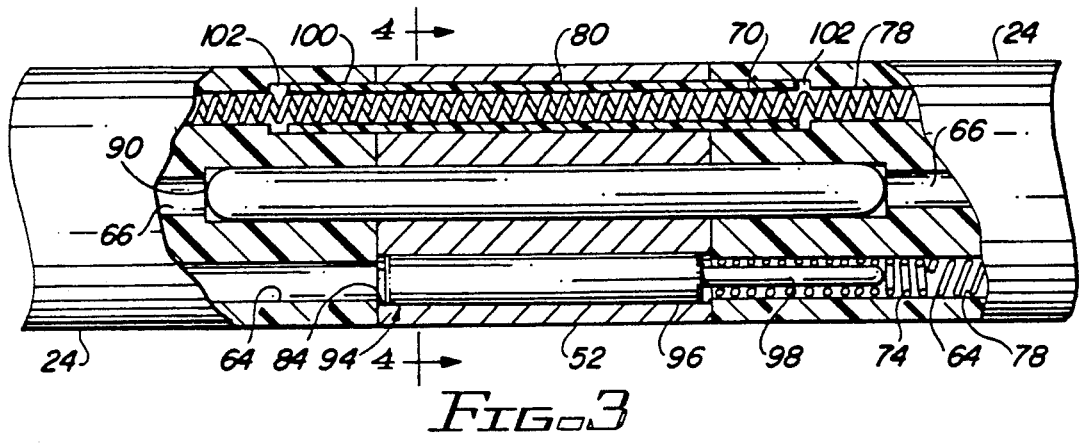
FIG. 3 is a generally axial cross-sectional view, depicting the connection between the multilumen tubing and the electrode.

FIG. 3 depicts an axial cross-sectional view of the assembled ring electrode 52 and multilumen tubing 24 illustrated in the exploded view of FIG. 2. Upon assembly of the respective components as illustrated in FIG. 3, the connection of the multilumen tubing 24 and the ring electrode 52 is stabilized by the stabilizing element 90 so that bending at the joint of the abutting faces of the multilumen tubing 24 and the ring electrode 52 is minimized due to the rigid nature of the stabilizing element 90 as well as the cylindrical insulating element 100 and the connecter pin 94.

The ring electrode 52 is depicted as having an axial length which is less than the axial length of the cylindrical insulating element 100 or the axial length of the stabilizing element 90. However, as discussed above, the length of the cylindrical insulating element 100 may be equal to the length of the ring electrode 52. However, it is preferred that the lengths of both the cylindrical insulating element 100 and the stabilizing element 90 are greater than the length of the ring electrode 52. The length of the stabilizing element is preferably in the range of between about 1.5 to 2.5 times the length of the ring electrode 52.

FIG. 3 also illustrates that the connector pin 94 has a head portion 96 having a diameter greater than the diameter of the passageway 78 within the conductor 74. Alternatively, the head portion 96 and tail portion 98 of the connecter pin 94 may be substantially uniform, and the diameter of bore 84 would be formed to match the outer diameter of the head portion 96 of the connecter pin 94. Preferably, the diameter of bore 84 through ring electrode 52 is substantially equal to the diameter of the lumen 64 and the connector pin 94 is designed to have a head portion 96 having a greater diameter than the tail portion 98.

Further, as also depicted in FIG. 3, the bore 80 through ring electrode 52, which accommodates the cylindrical insulating element 100, is preferably greater in diameter than the diameter of the respective lumen 60. This difference is equal to the wall thickness of the cylindrical insulating element 100, which has an internal diameter allowing pass-through of the conductor 70. It may also be appreciated that, for a multilumen tubing 24 which is configured to receive projecting end portions of the cylindrical insulating element 100, the respective lumen 60 must be drilled out to increase its inner diameter near the abutting face of the multilumen tubing 24 to allow the lumen 60 to receive the cylindrical insulating element 100.

Figure 4:
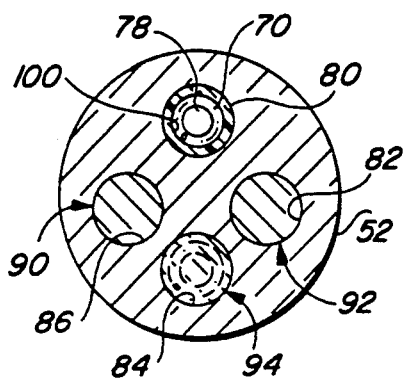
FIG. 4 is a cross-sectional view taken along lines 4—4 of FIG. 3, depicting the cylindrical electrode.

The relative diameters of the various components making up the connection between the multilumen tubing 24 and the ring electrode 52 may also be better understood from a review of FIG. 4, which is a cross-sectional view through the middle of the ring electrode 52. Therein, the ring electrode 52 is depicted as being a solid cross-sectional cylinder having the four axial bores 80, 82, 84, 86 therein. The axial bores 80, 82 and 86 in ring electrode 52 are configured to have diameters essentially equal to the diameter of the respective lumens 60, 62 and 66 (FIG. 2) which they abut. Moreover, it should be noted that while the foregoing discussion provides a detailed description of one stabilizer pin 90 which is disposed within the lumen 66 and axial bore 86, it may also be appreciated that the connection may be aided by having two stabilizer pins 90 and 92, positioned in the bores 86 and 82, respectively, as shown in the cross-section of FIG. 4, thereby providing additional stability to the connection.

Figure 5:
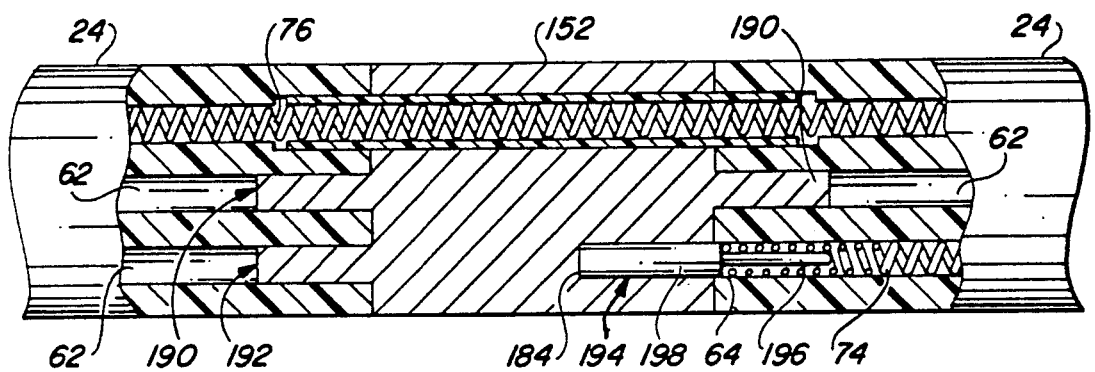
FIG. 5 is a first alternative embodiment of the ring electrode of FIG. 1.

FIG. 5 depicts an alternative embodiment of a ring electrode 152 wherein the ring electrode 152 is initially configured to have a projecting cylinder or stabilizing element 190 which performs the same function as the stabilizing pin 90 discussed above. The configuration shown in FIG. 5, wherein the ring electrode 152 is depicted as having a solid cylinder 190 projecting from one side and two solid cylinders 190, 192 projecting from the second side, provides enhanced stability to the interconnection. In the alternative embodiment of FIG. 5 the projecting solid cylinders 190, 192 insert into vacant lumens within the multilumen tubing 24.

In addition, the lumen 64 accommodates a conductor 74 terminating via a connection pin 194 to the ring electrode 152. The connection pin 194 has a tail portion 196 extending into the conductor 74 which is crimped or welded or cemented thereto within the lumen 64, and a head portion 198 which extends into a recess 184 within the ring electrode 152, and is electrically secured thereto. In addition, the ring electrode 152 may have the projecting cylinder 192 extending into the now vacant lumen 62 of the multilumen tubing 24 at the other side of the ring electrode 152 from the connection pin 194.

It should be noted that for all of the foregoing embodiments, the incorporation of the stabilizing element 90 or the projecting cylinders 190, 192 operates to seal off the empty lumen from invasion by body fluids. The elements can all be interconnected and bonded, by first coating them with an appropriate cement. Thus, the projecting portions of the stabilizing element 90 and cylinders 190, 192 will be solidly bonded to the internal surfaces of the vacant lumens. In this configuration, it is difficult for body fluids to invade the lumens even if the fluids invade the intersection between the facing portions of the multilumen tubing 24 and the ring electrode 52 (or 152).

Figure 6:
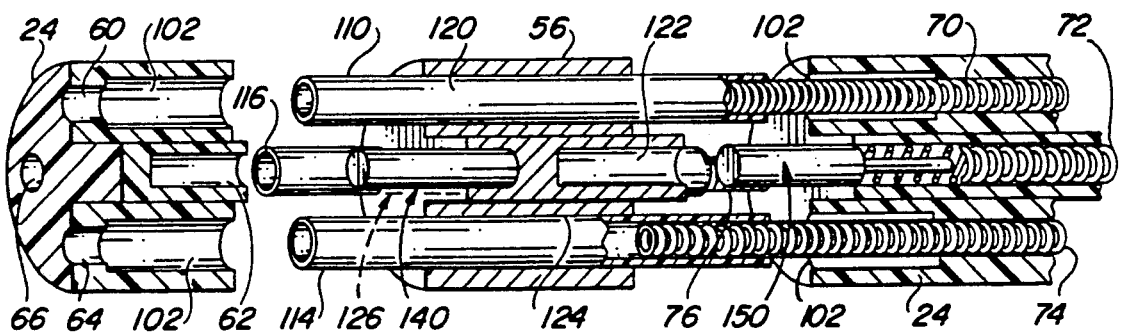
FIG. 6 is a second alternative embodiment of a ring electrode assembly.

For the ring electrode 56 in FIG. 1, it may be appreciated that there may be no vacant lumens to receive the stabilizing element 90. Accordingly, a different design for the ring electrode 56 may be required, as depicted in FIG. 6. The same design can also be incorporated for the ring terminal 38 of FIG. 1.

In FIG. 6, the electrode 56 includes a plurality of insulating cylinders 110, 114 and 116, which are preferably inserted into and through bores 120, 124, 126 defined within the ring electrode 56. The insulating cylinders 110, 114 and 116 require that the multilumen tubing 24 abutting the electrode 56 has the lumens 60, 64, 66 bored out to receive the insulating cylinders 110, 114, 116, respectively. These insulating cylinders allow pass-through of the respective electrical conductors 70, 74 and 76. It should also be noted that a projecting cylinder 140 can be designed to project from the ring electrode 56 (or it may be inserted into and project from a portion of the bore 122) to extend into the vacant lumen 62, opposite pin connector 150 in the ring electrode 56. By this configuration, the benefits of the reinforcing elements projecting from the ring electrode 56 into the multilumen tubing 24 are maximized.

In view of the foregoing detailed discussion, the present invention defines a method of constructing an in-line ring electrode in a pacing lead. The method includes cutting a preformed multilumen tubing having a plurality of lumens into at least two segments, and forming cylindrical electrodes having at least two axially extending bores corresponding to at least two of said lumens. These components are assembled by inserting at least two conductors through two of the lumens of at least one of said multilumen tubing segments, electrically interconnecting the cylindrical electrode to at least one of the two conductors, and interconnecting and affixing the cylindrical electrode between the multilumen tubing segments.

The step of interconnecting and affixing may include providing at least one connecting element projecting from the cylindrical electrode and inserted into at least one of the lumens of each of said respective multilumen tubing segments. The connecting element is preferably the stabilizer pin inserted through one of the bores of the cylindrical electrode.

The method of forming the pacing lead may further include inserting an insulating cylinder through one of the bores of the cylindrical electrode. The insulating cylinder projects from the cylindrical electrode into one of the lumens of the multilumen tubing. The insulating cylinder is configured to have an internal bore extending therethrough to accommodate pass-through of one of the electrical conductors insulated from the cylindrical electrode.

It should be evident from the foregoing description that the present invention provides many advantages in the field of implantable pacing leads. Although preferred embodiments are specifically illustrated and described herein, it will be appreciated that many modifications and variations of the present invention are possible in light of the above teaching to those skilled in the art. It is preferred, therefore, that the present invention be limited not by the specific disclosure herein, but only by the appended claims.

What is claimed is:

1. A pacing lead having a connector at a proximal end and an electrode at a distal end interconnected by a lead body, said pacing lead comprising:
   a multilumen tubing having a plurality of lumens;
   a plurality of conductors extending through said lumens of said multilumen tubing;
   at least one cylindrical electrode having a solid generally cylindrical cross section and at least two bores corresponding to two of said lumens;
   means for electrically interconnecting said at least one cylindrical electrode to at least one of said plurality of conductors; and
   means for interconnecting and affixing said at least one cylindrical electrode to said multilumen tubing, wherein said means for interconnecting and affixing includes a connecting element projecting from said cylindrical electrode for insertion into at least one of said lumens.

2. The pacing lead of claim 1, wherein said means for interconnecting and affixing further comprises:
   an adhesive material bonding said connecting element to said respective lumen.

3. The pacing lead of claim 2, wherein said connecting element comprises:
   a stabilizer pin inserted through one of said bores of said cylindrical electrode and extending therefrom into a vacant lumen of said multilumen tubing.

4. The pacing lead of claim 3, wherein said connecting element further comprises:
   an insulating cylinder inserted through one of said bores of said cylindrical electrode and projecting from at least one end of said cylindrical electrode, said projecting portion extending into said lumen of said multilumen tubing, said insulating cylinder having an internal bore extending therethrough to accommodate pass-through of one of said electrical conductors insulated from said cylindrical electrode.

5. The pacing lead of claim 2, wherein said connecting element comprises:
   at least one projecting cylinder formed integrally with said cylindrical electrode, said projecting cylinder being inserted into a respective lumen of said multilumen tubing.

6. The pacing lead of claim 5, wherein said connecting element further comprises:
   an insulating cylinder inserted through one of said bores of said cylindrical electrode and projecting from at least one end of said cylindrical electrode, said projecting portion extending into one of said lumens of said multilumen tubing, said insulating cylinder having an internal bore extending therethrough to accommodate pass-through of one of said electrical conductors insulated from said cylindrical electrode.

7. The pacing lead of claim 2, wherein said connecting element comprises:
   an insulating cylinder inserted into one of said bores of said cylindrical electrode and projecting from at least one end of said cylindrical electrode, said projecting portion extending into one of said lumens of said multilumen tubing, said insulating cylinder having an internal bore extending therethrough to accommodate pass-through of one of said electrical conductors insulated from said cylindrical electrode.

8. The pacing lead of claim 2, wherein said connecting element comprises:
   a pin connector having a head portion electrically connected to one of said bores of said cylindrical electrode, said pin connector also having a tail portion extending into one of said lumens and electrically connected to said conductor therein.

9. The pacing lead of claim 2, wherein said cylindrical electrode comprises:
   a cylinder of electrically conductive metallic material; and
   connector means for interconnecting one of said electrical conductors and said cylindrical electrode, said connector means including a pin connector having a head portion electrically connected to one of said bores of said cylindrical electrode, said pin connector also having a tail portion extending into one of said lumens and electrically connected to the conductor therein.

10. The pacing lead of claim 1, wherein said means for interconnecting and affixing includes at least one connecting element projecting from said cylindrical electrode and inserted into at least one of said lumens, said connecting element having a configuration defined by at least one of:
    (a) a stabilizer pin inserted through one of said bores of said cylindrical electrode and extending therefrom into a respective lumen of said multilumen tubing;
    (b) an insulating cylinder inserted through one of said bores of said cylindrical electrode and projecting from at least one end of said cylindrical electrode, said projecting portion extending into a respective lumen of said multilumen tubing, said insulating cylinder having an internal bore extending therethrough to accommodate pass-through of one of said electrical conductors insulated from said cylindrical electrode; or
    (c) a projecting cylinder formed integrally with said cylindrical electrode, said projecting cylinder being inserted into one of said lumens of said of multilumen tubing.

11. The pacing lead of claim 10, further comprising:
a pin connector having a head portion electrically connected to one of said bores of said cylindrical electrode, said pin connector also having a tail portion extending into one of said lumens and electrically connected to said conductor therein.

12. The pacing lead of claim 10, wherein said cylindrical electrode comprises:
a cylinder of electrically conductive metallic material; and
connector means for interconnecting one of said electrical conductors and said cylinder of metallic material, said connector means including a pin connector having a head portion electrically connected to one of said bores of said cylindrical electrode, said pin connector also having a tail portion extending into said lumen and electrically connected to the conductor therein.

13. A pacing lead having a connector at a proximal end and an electrode at a distal end interconnected by a lead body, said pacing lead comprising:
a multilumen tubing having at least three lumens;
a conductor extending through each of said at least three lumens of said multilumen tubing;
at least one cylindrical electrode having at least three bores corresponding to said at least three lumens, wherein said cylindrical electrode includes:
a cylinder of electrically conductive metallic material; and
connector means for interconnecting one of said electrical conductors and said cylindrical electrode;
means for electrically interconnecting said at least one cylindrical electrode to at least one of said conductors; and
means for interconnecting and affixing said at least one cylindrical electrode to said multilumen tubing.

14. The pacing lead of claim 13, wherein said connector means comprises:
a pin connector having a head portion electrically connected to one of said bores of said cylindrical electrode, said pin connector also having a tail portion extending into one of said lumens and electrically connected to said conductor therein.

15. A pacing lead having a connector at a proximal end and an electrode at a distal end interconnected by a lead body, said pacing lead comprising:
a multilumen tubing having a plurality of lumens;
a plurality of conductors extending through said lumens of said multilumen tubing;
at last one cylindrical electrode of electrically conductive material, said cylindrical electrode having at least one bore corresponding to at least one of said lumens;
a connector element interconnecting one of said electrical conductors and said cylindrical electrode, said connector element having a head portion electrically connected to one of said bores of said cylindrical electrode and a tail portion extending into one of said lumens and electrically connected to said conductor therein; and
at least one connecting element projecting from said cylindrical electrode and inserted into at least one of said lumens, said connecting element bonded to said lumen, said connecting element having a configuration defined by at least one of:

(a) a stabilizer pin inserted through one of said bores of said cylindrical electrode and extending therefrom;
(b) an insulating cylinder inserted through one of said bores of said cylindrical electrode and projecting from at least one end of said cylindrical electrode into said lumen of said multilumen tubing, said insulating cylinder having an internal bore extending therethrough to accommodate pass-through of one of said electrical conductors insulated from said cylindrical electrode; or
(c) a projecting cylinder formed integrally with said cylindrical electrode, said projecting cylinder being inserted into said lumen of said of multilumen tubing.

16. A method of constructing an in-line ring electrode in a pacing lead having a connector at a proximal end and an electrode at a distal end interconnected by a lead body, the method comprising:
providing at least two segments of a preformed multilumen tubing having a plurality of lumens;
inserting at least two conductors through two of said lumens of at least one of said multilumen tubing segments;
providing at least one cylindrical electrode having at least two axially extending bores corresponding to at least two of said lumens;
electrically interconnecting said at least one cylindrical electrode to at least one of said two conductors; and
interconnecting and affixing said at least one cylindrical electrode between said at least two multilumen tubing segments wherein said step of interconnecting and affixing includes providing at least one connecting element projecting from said cylindrical electrode and inserted into at least one of said lumens of each of said respective multilumen tubing segments.

17. The method of constructing the pacing lead of claim 16, wherein said connecting element is a stabilizer pin inserted through one of said bores of said cylindrical electrode and extending therefrom into a respective lumen of said multilumen tubing.

18. The method of constructing the pacing lead of claim 17, further comprising:
inserting an insulating cylinder through one of said bores of said cylindrical electrode, said insulating cylinder projecting from at least one end of said cylindrical electrode into one of said lumens of said multilumen tubing, said insulating cylinder having an internal bore extending therethrough to accommodate pass-through of one of said electrical conductors insulated from said cylindrical electrode.

19. A method of constructing a pacing lead having a lead body interconnecting a connector at a proximal end and an electrode at a distal end, the method comprising:
providing a number of segments of multilumen tubing having a plurality of lumens extending therethrough;
inserting a plurality of electrical conductors through at least one of said lumens of each of said segments of multilumen tubing;
forming at least one cylindrical electrode from an electrically conductive material, said cylindrical electrode having at least one bore formed axially therethrough in a location corresponding to at least one of said lumens of said multilumen tubing segments;

interconnecting at least one of said electrical conductors and said cylindrical electrode; and providing at least one connecting element projecting from said cylindrical electrode and inserted into at least one of said lumens, said connecting element bonded to said lumen, said connecting element being defined by at least one of:

(a) a stabilizer pin inserted through one of said bores of said cylindrical electrode and extending therefrom;

(b) an insulating cylinder inserted through one of said bores of said cylindrical electrode and projecting from at least one end of said cylindrical electrode into said lumen of said multilumen tubing, said insulating cylinder having an internal bore extending therethrough to accommodate pass-through of one of said electrical conductors insulated from said cylindrical electrode; or (c) a projecting cylinder formed integrally with said cylindrical electrode, said projecting cylinder being inserted into said lumen of said of multilumen tubing.

* * * * *